United States Patent
Jones et al.

(10) Patent No.: US 8,377,104 B2
(45) Date of Patent: Feb. 19, 2013

(54) DUAL ACTION ROD REDUCING AND LOCKING DEVICE AND METHOD

(75) Inventors: Scott A Jones, McMurray, PA (US); Michael Barrus, Ashburn, VA (US); Andy Rock, Spring Grove, PA (US)

(73) Assignee: K2M, Inc., Leesburg, VA (US)

( * ) Notice: Subject to any disclaimer, the term of this patent is extended or adjusted under 35 U.S.C. 154(b) by 141 days.

(21) Appl. No.: 13/069,777

(22) Filed: Mar. 23, 2011

(65) Prior Publication Data

US 2011/0224733 A1    Sep. 15, 2011

Related U.S. Application Data

(62) Division of application No. 11/526,880, filed on Sep. 26, 2006, now Pat. No. 7,931,654.

(60) Provisional application No. 60/780,596, filed on Mar. 9, 2006.

(51) Int. Cl.
*A61B 17/88* (2006.01)
*A61B 17/70* (2006.01)

(52) U.S. Cl. ...................... 606/279; 606/86 A (58) Field of Classification Search .......... 606/264–279, 606/86 A See application file for complete search history.

(56) References Cited

U.S. PATENT DOCUMENTS

| | | |
|---|---|---|
| 5,020,519 A | 6/1991 | Hayes et al. |
| 5,910,141 A | 6/1999 | Morrison et al. |
| 6,790,209 B2 | 9/2004 | Beale et al. |
| 7,160,300 B2 | 1/2007 | Jackson |
| 2005/0192570 A1 | 9/2005 | Jackson |
| 2005/0261702 A1 | 11/2005 | Oribe et al. |
| 2006/0089651 A1 | 4/2006 | Trudeau et al. |
| 2006/0200132 A1 | 9/2006 | Chao et al. |
| 2007/0016192 A1 | 1/2007 | Woods |
| 2007/0093817 A1 | 4/2007 | Barrus et al. |
| 2007/0093849 A1 | 4/2007 | Jones et al. |

*Primary Examiner* — Ellen C Hammond

(74) *Attorney, Agent, or Firm* — Carter, DeLuca, Farrell & Schmidt, LLP (57) ABSTRACT

Provided is a dual action surgical instrument for use in orthopedic surgical procedures that is capable of reducing a rod into position in a rod receiving notch in the head of a bone screw with a first action and subsequently locking the rod into the receiving notch by a second action of the same instrument. A method of using the device is also provided.

20 Claims, 8 Drawing Sheets

SECTION C-C
SCALE 2 : 1

FIG. 6D

SECTION B-B
SCALE 2 : 1

FIG. 6C

SECTION A-A
SCALE 2 : 1

SECTION F-F
SCALE 2:1
FIG. 7D

SECTION E-E
SCALE 2:1
FIG. 7C

SECTION D-D
SCALE 2:1
FIG. 7B

DUAL ACTION ROD REDUCING AND LOCKING DEVICE AND METHOD

CROSS-REFERENCE TO RELATED APPLICATIONS

The present application is a divisional of U.S. patent application Ser. No. 11/526,880, filed on Sep. 26, 2006, which claims the benefit of and priority to U.S. Provisional Patent Application No. 60/780,596, filed Mar. 9, 2006, the entire contents of which are incorporated by reference herein.

BACKGROUND

1. Technical Field

The present invention relates to orthopedic surgery and in particular to devices for stabilizing and fixing the bones and joints of the body. Particularly, the present invention relates to a dual action instrument capable of reducing a rod into position in a rod receiving notch in the head of a bone screw with a first action and subsequently locking the rod into that receiving notch by a second action of the same instrument.

2. Background of Related Art

The spinal column is a complex system of bones and connective tissues that provides support for the human body and protection for the spinal cord and nerves. The human spine is comprised of thirty-three vertebrae at birth and twenty-four as a mature adult. Between each pair of vertebrae is an intervertebral disc, which maintains the space between adjacent vertebrae and acts as a cushion under compressive, bending and rotational loads and motions.

There are various disorders, diseases and types of injury, which the spinal column may experience in a lifetime. The problems may include but are not limited to scoliosis, kyphosis, excessive lordosis, spondylolisthesis, slipped or ruptured disc, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure known as spinal fusion. A spinal fusion procedure involves fusing two or more vertebral bodies in order to eliminate motion at the intervertebral disc or joint. To achieve this, natural or artificial bone, along with a spacing device, replaces part or all of the intervertebral disc to form a rigid column of bone, which is stabilized by mechanical hardware.

The mechanical hardware used to immobilize the spinal column typically involves a series of bone screws and metal rods or plates. When the spine surgery is posteriorly performed, it is common practice to place bone screws into the vertebral bodies and then connect a metal rod between adjacent vertebral bodies. When the spine surgery is performed anteriorly, it is common practice to attach a thin metal plate directly to the vertebral bodies and secure it to each vertebral level using one or more bone screws.

The process of properly inserting the spinal rod into the receiving slot of a bone screw and then securing that connecting rod in place often can require that the surgeon use a number of instruments and expend a great deal of time and effort to accomplish the task. When bone screws in several adjacent vertebrae are to be securely connected by a spinal rod, the repeated process of inserting the rod into the heads of the one screws and then securing the rod in place for each respective bone screw can be difficult, tiresome and time consuming. It is therefore important that an instrument be provided that is specifically designed to facilitate the process for the surgeon such that the connecting rod can be easily and quickly inserted into each bone screw and with minimal effort and loss of time. It is also desirable that the rod be secured into position in the bone screw head without the application of additional torsional force to the bone screw and the bone into which it is attached.

Conventional efforts to meet this need have fallen short in that no single instrument has been provided that effectively positions and inserts a connecting rod into position in the receiving slot of the head of a bone screw and also provides a torque-free locking action to secure the rod in place.

For these reasons there remains a need for a device which, can with a single action first securely grasp the head of a bone screw and accomplish the reduction of a posteriorly introduced rod into the head of that bone screw and in a second simple action provide a torque-free locking process of the rod into the bone screw head.

SUMMARY

In accordance with an embodiment of the present disclosure, there is provided a method of reducing a rod into a taper lock bone screw and locking the rod into place. The method includes providing a rod reducer including an elongate body having a bone screw grasping element, a rod reducing sleeve circumferentially disposed around at least a portion of the elongate body, a rod reducing lever coupled to the rod reducing sleeve, a locking sleeve circumferentially disposed around at least a portion of the rod reducing sleeve, and a locking lever coupled to the locking sleeve. In particular, the rod reducing sleeve includes a rod contact portion. The rod reducing lever is configured to actuate the grasping element to grasp the screw and position the rod into a rod receiving notch in the taper lock bone screw. In addition, the locking sleeve includes a screw grasping structure. The locking lever is configured to actuate the screw grasping structure to grasp an outer sleeve of the taper lock bone screw and move the outer sleeve into a locked position. The method further includes implanting the taper lock bone screw into a bone of a subject, placing the rod in the rod reducer, aligning the rod reducer with the taper lock bone screw, reducing the rod into the rod receiving notch in the taper lock bone screw, and locking the rod into place.

In another embodiment, aligning the rod reducer with the taper lock bone screw may include inserting at least a portion of the taper lock bone screw into the rod reducer.

In still another embodiment, the rod reducing lever may be pivotally associated with the elongate body and the rod reducing sleeve.

In still another embodiment, reducing the rod into the rod receiving notch in the taper lock bone screw may include actuating the rod reducing lever causing grasping element to grasp the taper lock bone screw and rod contact portion to position the rod into the rod receiving notch of the taper lock bone screw.

In still another embodiment, actuating the rod reducing lever may include aligning the rod reducing lever with the elongate body.

In still another embodiment, locking the rod into place may include actuating the locking lever causing the screw grasping structure to grasp and move the outer sleeve into a lock position.

In still another embodiment, actuating the locking lever may include aligning the rod reducing lever with the elongate body.

In still another embodiment, the rod reducer may further include a first connecting arm pivotally connecting the rod reducing lever with the rod reducing sleeve.

In still another embodiment, the rod reducer may further include a second connecting arm pivotally connecting the locking sleeve with the locking lever.

In still another embodiment, the locking sleeve may define a longitudinal slit.

In still yet another embodiment, locking the rod into place may include sliding the outer sleeve of the taper lock bone screw into a partially locked position.

In accordance with another embodiment of the present disclosure, there is provided a method of reducing a rod into a taper lock bone screw and locking the rod into place. The method includes providing a spinal fixation system including a taper lock bone screw and a rod reducer. In particular, the taper lock bone screw includes an inner housing and an outer housing surrounding at least a portion of the inner housing. The inner housing defines a rod receiving notch, and the outer housing is movable relative to the inner housing. The rod reducer includes an elongate body having a bone screw grasping element, a rod reducing sleeve circumferentially disposed around at least a portion of the elongate body, a rod reducing lever coupled to the rod reducing sleeve, a locking sleeve circumferentially disposed around at least a portion of the rod reducing sleeve, and a locking lever coupled to the locking sleeve. The rod reducing sleeve includes a rod contact portion. The rod reducing lever is configured to actuate the grasping element to grasp the screw and position the rod into the rod receiving notch defined in the taper lock bone screw. In addition, the locking sleeve includes a screw grasping structure. The locking lever is configured to actuate the screw grasping structure to grasp an outer sleeve of the taper lock bone screw and move the outer sleeve into a locked position.

The method further includes implanting the taper lock bone screw into a vertebral body of a subject, placing the rod in the rod reducer, aligning the rod reducer with the taper lock bone screw, reducing the rod into the rod receiving notch in the inner housing of the taper lock bone screw, and locking the rod into place.

In another embodiment, locking the rod into place may include sliding the outer sleeve of the taper lock bone screw into a partially locked position.

BRIEF DESCRIPTION OF THE DRAWINGS

The foregoing and other features of the disclosed device will become apparent to one skilled in the art to which the present invention relates upon consideration of the following description of exemplary embodiments with reference to the accompanying drawings, wherein.

DETAILED DESCRIPTION OF EMBODIMENTS

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are nonlimiting, but serve merely as a basis for the invention as defined by the claims provided herewith. The device described below can be modified as needed to conform to further development and improvement of materials without departing from the inventor's concept of the invention as claimed.

The device, as generally shown at 10 in all of the accompanying figures is a dual action rod reducing and locking device that requires only the sequential movement of two separate activation levers on a single instrument to first position a rod into the head of a bone screw and second to lock the rod into place in the head of the bone screw. The device is an elongated multi-layered tubular instrument that includes an elongated central structure 12 about which at certain positions other components of the device 10 are either attached or circumferentially disposed. The central structure 12 can be tubular with a central structure lumen 14 extending from a central structure first end 16 to a central structure second end 18. The central structure lumen 14 can be sized to permit the passage of other instruments as needed.

An upper portion of the central structure 12 that terminates at or near the central structure first end 16 is configured to serve as a handle 20 for the device 10. The handle 20 of the device extends from a position near the first end 16 to position that approaches toward the central portion of the device 10. Immediately adjacent to the central structure 12 and circumferentially disposed around at least a portion of the lower part of the central structure 12 is a rod reducing sleeve 22 that is sized and configured to freely move along the longitudinal axis of the device 10. As with all of the components of the device 10, the rod reducing sleeve 22 is constructed to be as thin and light weight as possible to facilitate insertion of the device into the surgical site and to promote ease of manual use of the device; however, the structure of the rod reducing sleeve 22 is strong enough to maintain its integrity during the rod reducing process of the device 10 when the rod reducing sleeve 22 will be forced into contact with a rod and must then transfer manual force against the rod so as to position it into a receiving notch in the head of a bone screw. The rod reducing sleeve 22 is sufficiently long so as to extend from a position below the handle 20 of the device 10 to a position at or near the second end 16 of the central structure 12.

Figure 1A:
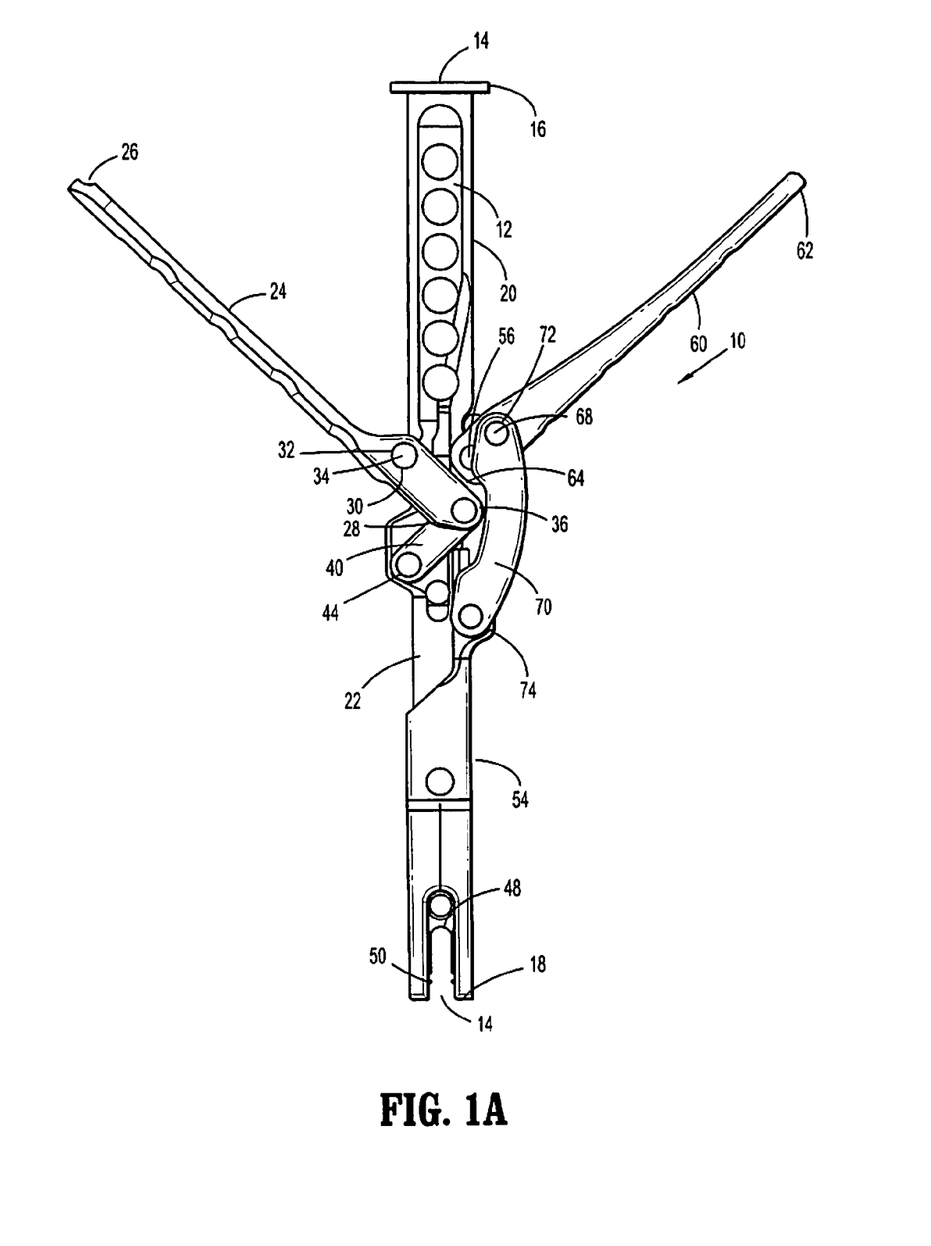
FIGS. 1A-B respectively show a side view and a top view of the dual action rod reducing and locking device in an open position; that is the first actuation lever is in an open position and if activated can effect the bone screw head grasping process and the rod reducing process. The second actuation lever is an open position and if activated can effect the process of locking the rod into position in the bone screw head after the rod has been so positioned.
Figure 1B:
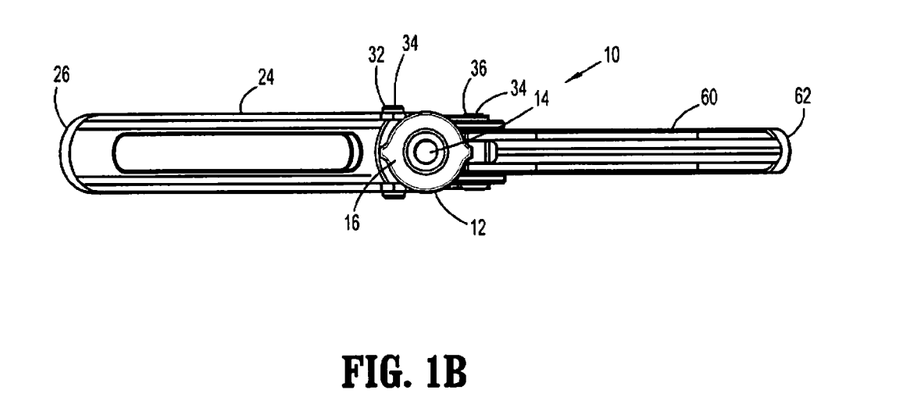
Figure 2A:
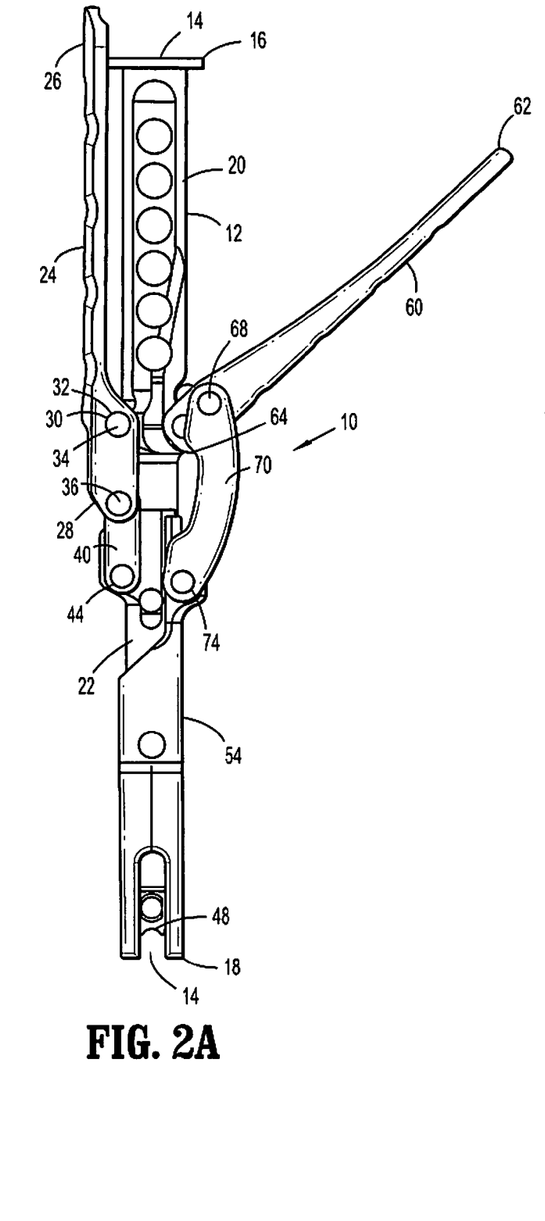
FIGS. 2A-B respectively show a side view and a top view of the dual action rod reducing and locking device having the first actuation lever in a closed position; that is the first actuation lever is in a closed position and having been moved inward it has effected the bone screw head grasping process and the rod reducing process. The second actuation lever is in an open position and if activated can effect the process of locking the rod into position in the bone screw head after the rod has been so positioned.
Figure 2B:
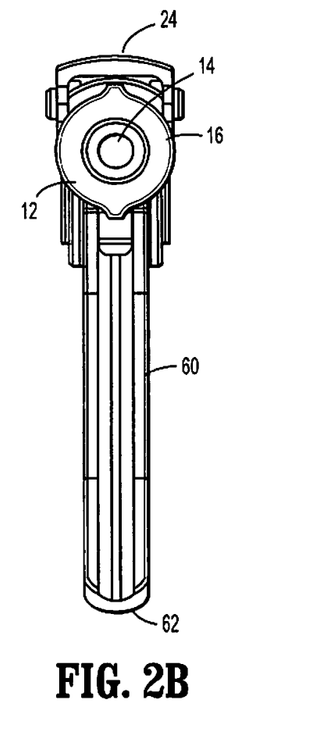
Figures 3A, 3B, 3C:
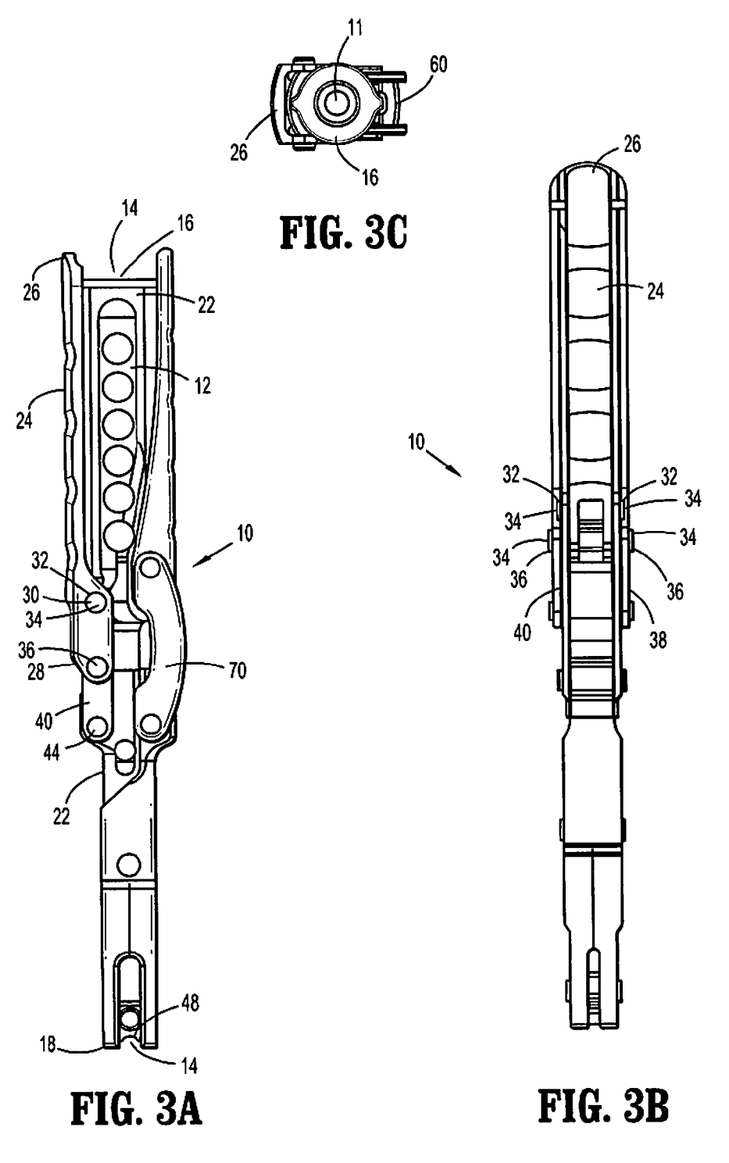
FIGS. 3A-C respectively show a side, back, and top view of the dual action rod reducing and locking device in a closed position; that is the first actuation lever is in a closed position and having been moved inward it has effected the bone screw head grasping process and the rod reducing process. The second actuation lever is in a closed position; that is having been moved inward it has effected the process of locking the rod into position in the bone screw head after it had been so positioned.

A rod reducing actuator 24, as shown in the exemplary embodiment of FIGS. 1A-B, 2A-B, 3A-C, 4, 5A, and 6A, is preferably configured as a lever although other actuating devices can also be used. The rod reducing actuator 24 has a first end 26 that, when in an open position, as shown in FIGS. 1A-B can be extended away from or laterally from the device 10 and a rod reducing actuator 24 second end 28, that is generally more medially directed to the device 10. Preferably the rod reducing actuator 24 is pivotally attached to the central structure 12 at rod reducer first pivot point 30 provided at a position approximate to the lower portion of the handle 20 of the device 10. The rod reducer first pivot point 30 of the central structure 12 corresponds to the actuator pivot point 32, both of which are preferably pivot pin holes that are defined respectively in the central structure 12 and the rod reducing actuator 24 and connected by a pivot pin 34. It is however, within the inventor's concept that any pivoting mechanism, such as a dimple and corresponding protrusion, can be used instead of the preferred pivot pin 34. It is also within the inventors' concept that the rod reducer first pivot point 30 can be positioned anywhere along the length of the central structure 12 as long as effective leverage for the rod reducing actuator 24 can be achieved.

As shown in FIGS. 1A-B, 2A, 3A-C, 4, 5A, and 6A between the rod reducer first pivot point 32 and the rod reducing actuator second end 28 is a rod reducer second pivot point 36 that is pivotally connected to a first end 38 of a rod reducer connecting arm 40. As with all pivot points of the device, a pivot pin 34, as is well known in the art, is preferably used. Approximate to a second end 42 of the rod reducing connecting arm 40 is a rod reducing connecting arm second pivot point 44, which is pivotally connected to a rod reducing sleeve pivot point 46 located near the upper portion of the rod reducing sleeve 22.

The pivotal connections of the rod reducing actuator 24 to the central structure 12, the rod reducing connecting arm 40, and finally to the rod reducing sleeve 22, as shown in FIG. 1A have the effect of pulling the rod reducing sleeve 22 upward along the outside of the central structure 12 when the first end 26 of the rod reducing actuator lever 24 is pulled away or opened away from the longitudinal axis of the central structure 12. Conversely, as best shown in FIGS. 2A, 3A, 5A and 6A, when the rod reducing actuator lever 24 is squeezed by a surgeon so as to close the actuator lever 24 against the handle 20 of the central structure 12 the rod reducing sleeve 22 is forced downward toward the second end 18 of the central structure 12.

As shown in FIGS. 1A, 2A, 3A, 4, 5A and 6A, the rod reducing sleeve 22, at its lowest end near the second end of the central structure 12, is configured to provide a rod contact point 48 that preferably, as shown in the examples, will have a concave geometry complimentary to the arching shape of a rod cross-section.

Figure 4:
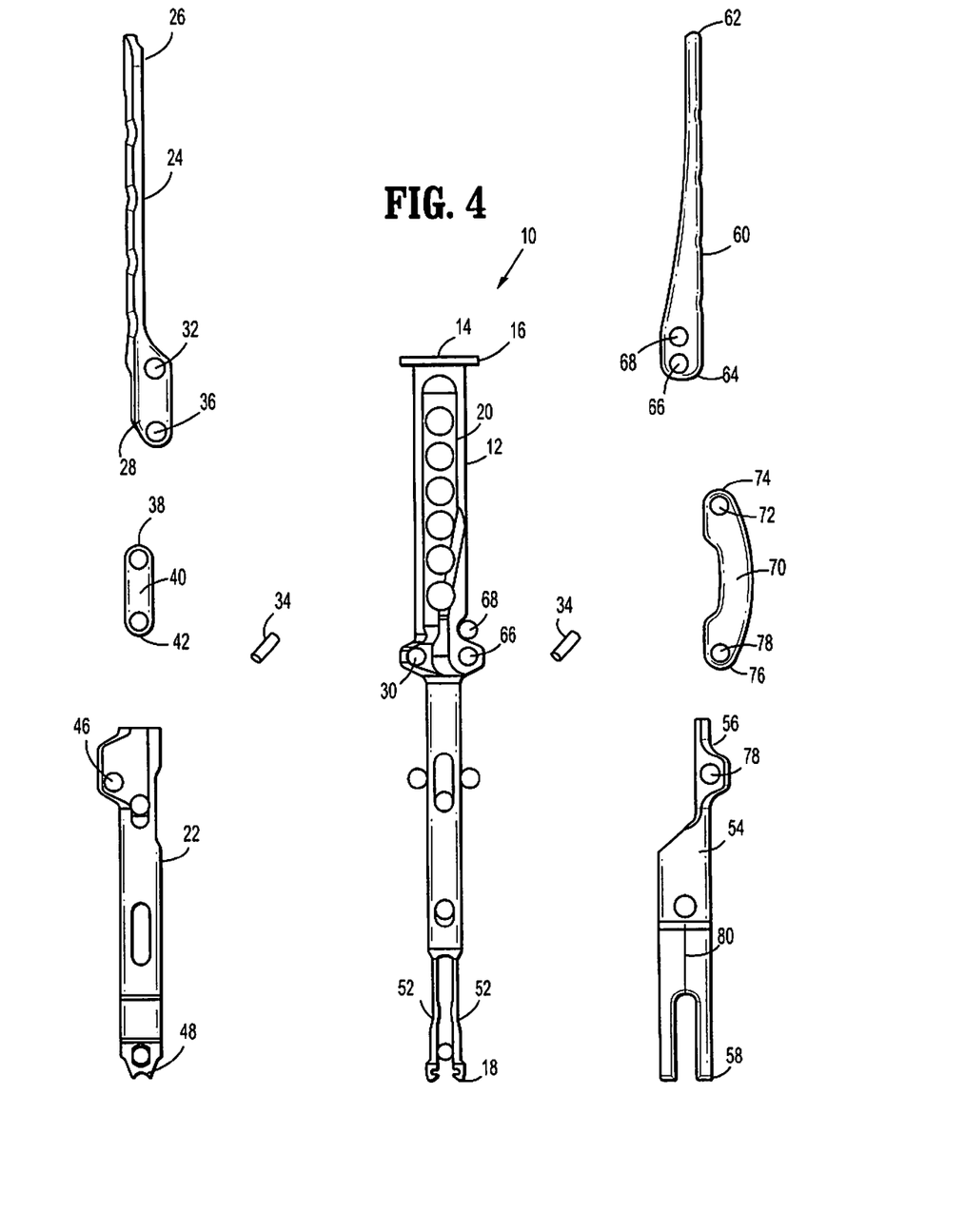
FIG. 4 shows the disassembled dual action rod reducing and locking device from a side perspective.
Figure 5A:
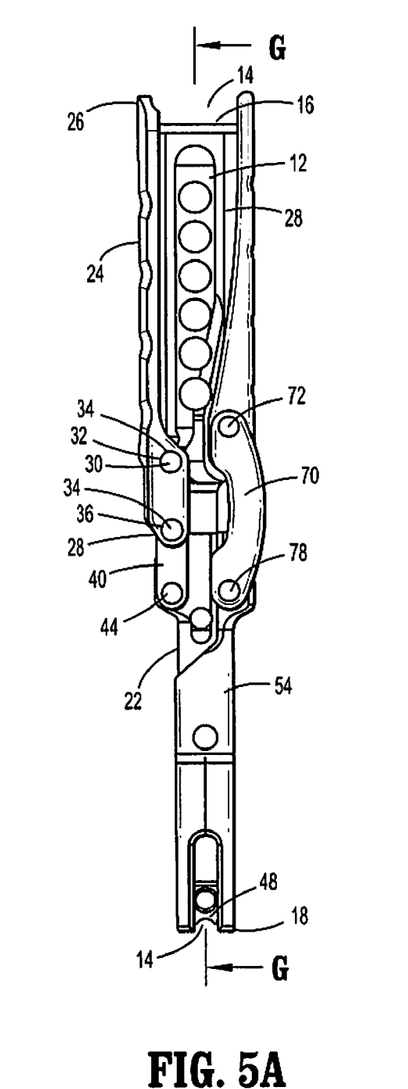
FIGS. 5A-B respectively show a side view and a cross-sectional view along the longitudinal axis of the dual action rod reducing and locking device in a closed position.
Figure 5B:
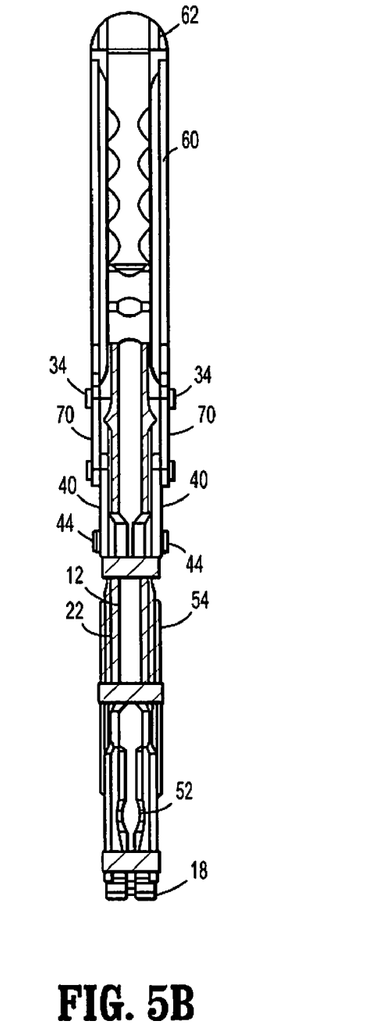
Figure 6A:
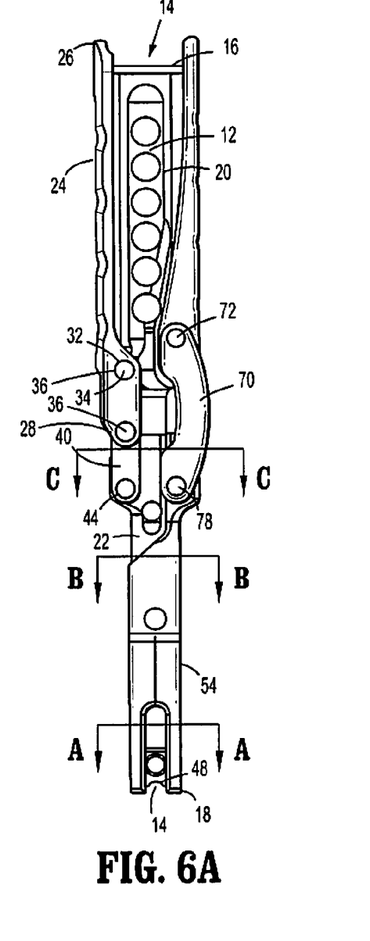
FIGS. 6A-D respectively show a side view, and cross-sectional views along the transverse axis at different levels along the length of the dual action rod reducing and locking device in a closed position.
Figure 6B:
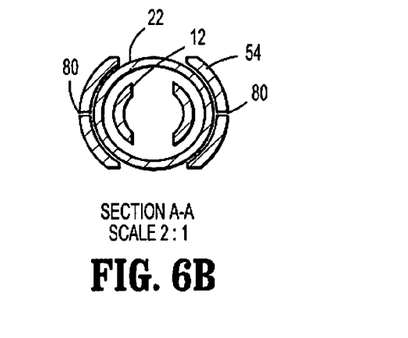
Figure 6C:
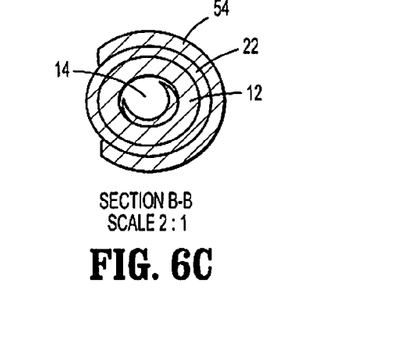
Figure 6D:
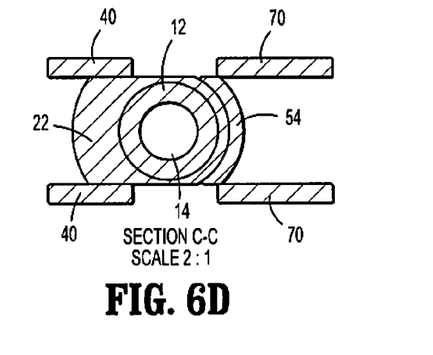
Figure 7A:
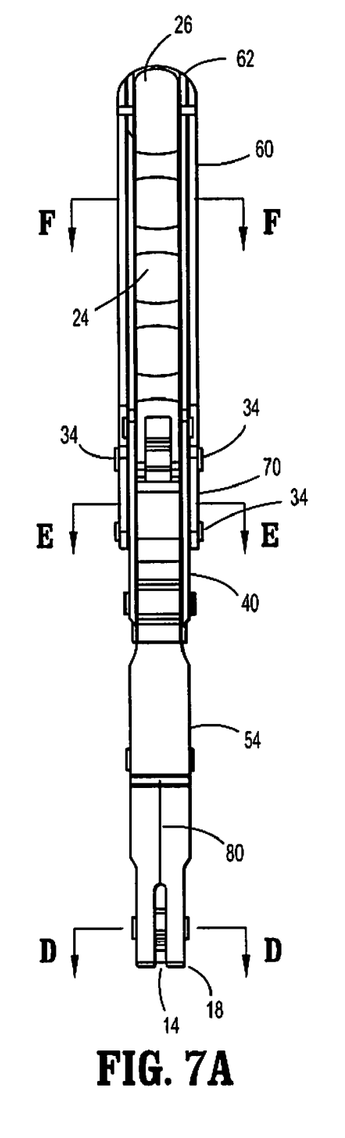
FIGS. 7A-D respectively show a back view and cross-sectional views along the transverse axis at different levels along the length of the dual action rod reducing and locking device in a closed position.
Figure 7B:
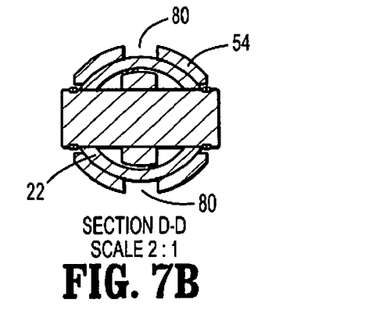
Figure 7C:
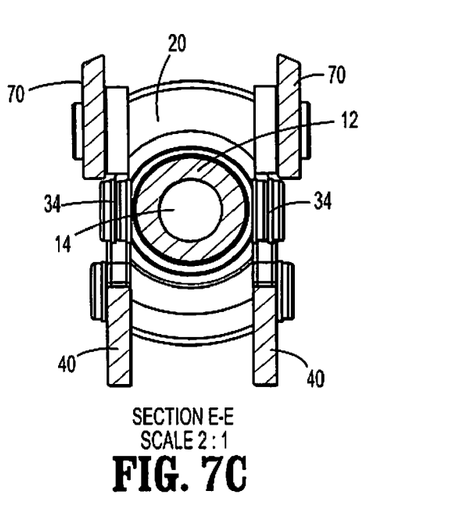
Figure 7D:
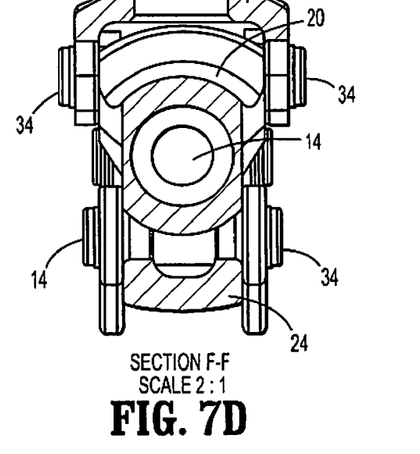

As shown in FIG. 4 the second end 18 of the central structure 12 terminates in at least one screw head grasping element 50 that is configured to grasp corresponding structures on the head of the bone screw into which the rod is to be positioned and locked. As shown in FIG. 4 the central structure diameter is widened or increased just above the grasping elements 50 to form central structure cam surfaces 52 such that as the rod reducing sleeve 22 is moved downward around the outside of the central structure 12, the inner wall of the rod reducing sleeve 22 can forcibly and compressively contact the cam surfaces 52 of the central structure thus forcing the screw head grasping elements inward into an engaging relationship with a properly positioned screw head.

Thus, when the surgeon activates the rod reducing actuator lever 24 by squeezing it inward against the handle 20 of the central structure 12 and the rod reducing sleeve 22 is forced downward, screw head grasping elements 50 engage and hold the screw head in place while the rod reducing sleeve and its terminal rod contacting point make forcible contact with a properly positioned rod such that as the screw head is held stationary, the rod is forced downward into position with a rod receiving notch of that screw head. A screw head having a rod receiving notch as well as appropriately configured corresponding grasping element receiving structures on the head of the bone screw is disclosed in commonly assigned U.S. patent application Ser. Nos. 11/493,624 and 11/493,625, the complete disclosures of which are fully incorporated herein by reference.

Upon completing the first action of the dual action device 10, that of grasping the screw head and reducing the rod into position in the screw head, the surgeon can then initiate the second action of the device, that of locking the rod in position in the screw head.

To accomplish this second action, the device 10 is provided with a locking sleeve 54 that is circumferentially disposed around at least a portion of the rod reducing sleeve 22. The locking sleeve 54 is sized to freely moved upward or downward along the longitudinal axis of the device 10. The locking sleeve has a locking sleeve first end 56 approximately at the level of the upper portion of the rod reducing sleeve and a locking sleeve second end 58 approximately at the level of the central structure second end 18.

A locking actuator, 60, which is preferably in the form of a lever actuator as shown in FIGS. 1A-B, 2A-B, 3A-B, 4, 5A-B, 6A and 7A, can be provided and pivotally attached to the opposite side of the central structure 12 from the rod reducing actuator 24. The locking actuator 60 can have a locking actuator first end 62 that when in the open position as shown in FIGS. 1A-B is located away from or lateral from the central structure 12 and a locking actuator second end 64 that is located more medial to the central structure 12. The locking actuator 60 is pivotally attached to the central structure 12 at a locking actuator first pivot point 66 that is at or near the second end of the locking actuator 60. At a position between the first pivot point 66 and the locking actuator first end 62, the locking actuator 60 is provided with a second pivot point 68 that is pivotally attached to a locking actuator connecting arm 70 at a locking connecting arm first pivot point 72. The locking connecting arm 70 has a locking connecting arm first end 74 and a locking connecting arm second end 76. At or near the locking actuator second end 76 is a connecting arm second pivot point 78. Pivotally connected to the locking actuator connecting arm 70 at the second pivot point 78 is upper portion of the locking sleeve 54.

The pivotal connections disclosed above for the locking actuator 60 to the locking actuator connecting arm 70 and finally to the locking sleeve 54 are such that when a surgeon squeezes the locking actuator lever 60 inward to a closed position adjacent to the handle 20, as shown in FIGS. 3A-B, 5A-B, 6A and 7A, the activation force is transmitted to the locking sleeve 54 so as to pull it upward along the outside of the rod reducing sleeve 22.

The locking sleeve 54 is provided with at least one expansion slit 80 that extends from the locking sleeve second end 58 upward along the longitudinal axis of the device for a portion of the total length of the locking sleeve 54. The second end of the locking sleeve 54 is configured to slip fit over the external surface of a bone screw head and to engage complimentary structures on the bone screw head such that when the locking actuator 60 is squeezed inward to a closed position and the locking sleeve 54 is pulled upward, the inward bias of the locking sleeve 54 will maintain an inward holding pressure on the outer sleeve of the bone screw head and in doing so pull the outer sleeve of the taper lock bone screw upward while the rod reducing sleeve 22 holds the inner portion of the taper lock bone screw in place. The effect of this holding and pulling action caused by the squeezing of the locking actuator lever 60 is that the outer sleeve of the taper lock screw will produce compressive forces against the rod contained within the head of the taper lock screw and it will thereby be locked into position.

It is the inventors' understanding that a partial squeezing movement of the locking actuator lever 60 will result in a partial compressive force on the taper lock screw and as such can provide a partial lock position that can allow for some adjustment of the relative position of the rod and screw one to the other. After any such adjustment is made, the locking actuator 60 can be moved fully inward into a closed or fully locked position. Upon completion of the second action of locking the rod into position, the device 10 can be released from its grasp of the screw and removed from the surgical site. When used, the partial lock position can be identified by the surgeon by providing a visual cue or indicia on the locking actuator lever 60 or by providing tactile or audible feedback to the user as the locking actuator 60 moves the mechanism past a cam or other frictional contact provided within the mechanism The device 10 can be manufactured as integral components by methods known in the art, to include, for example, molding, casting, forming or extruding, and machining processes. The components can be manufactured using materials having sufficient strength, resiliency and biocompatibility as is well known in the art for such devices. By way of example only, suitable materials cam include implant grade metallic materials, such as titanium, cobalt chromium alloys, stainless steel, or other suitable materials for this purpose.

It is also within the concept of the present invention to provide a kit, which includes the dual action device disclosed herein. Additionally, a kit can include two or more screws adaptable for use with the disclosed device, such as the taper lock screw disclosed and claimed in the commonly assigned and fully incorporated U.S. patent application Ser. Nos. 11/493,624 and 11/493,625. In addition the kit can contain surgical rods, such as, for example spinal rods. Additional devices such as cross-connectors, hooks, or links can also be included in the kit. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. A method of reducing a rod into a taper lock bone screw and locking the rod into place, the method comprising:
   providing a rod reducer including:
      an elongate body having a bone screw grasping element;
      a rod reducing sleeve circumferentially disposed around at least a portion of the elongate body, the rod reducing sleeve including a rod contact portion;
      a rod reducing lever coupled to the rod reducing sleeve, the rod reducing lever configured to actuate the grasping element to grasp the screw and position the rod into a rod receiving notch in the taper lock bone screw;
      a locking sleeve circumferentially disposed around at least a portion of the rod reducing sleeve, the locking sleeve including a screw grasping structure; and
      a locking lever coupled to the locking sleeve, the locking lever configured to actuate the screw grasping structure to grasp an outer sleeve of the taper lock bone screw and move the outer sleeve into a locked position;
   implanting the taper lock bone screw into a bone of a subject;
   placing the rod in the rod reducer;
   aligning the rod reducer with the taper lock bone screw;
   reducing the rod into the rod receiving notch in the taper lock bone screw; and
   locking the rod into place.

2. The method according to claim 1, wherein aligning the rod reducer with the taper lock bone screw includes inserting at least a portion of the taper lock bone screw into the rod reducer.

3. The method according to claim 1, wherein the rod reducing lever is pivotally associated with the elongate body and the rod reducing sleeve.

4. The method according to claim 3, wherein reducing the rod into the rod receiving notch in the taper lock bone screw includes actuating the rod reducing lever causing grasping element to grasp the taper lock bone screw and rod contact portion to position the rod into the rod receiving notch of the taper lock bone screw.

5. The method according to claim 4, wherein actuating the rod reducing lever includes aligning the rod reducing lever with the elongate body.

6. The method according to claim 3, wherein locking the rod into place includes actuating the locking lever causing the screw grasping structure to grasp and move the outer sleeve into a lock position.

7. The method according to claim 6, wherein actuating the locking lever includes aligning the rod reducing lever with the elongate body.

8. The method according to claim 1, wherein the rod reducer further includes a first connecting arm pivotally connecting the rod reducing lever with the rod reducing sleeve.

9. The method according to claim 1, wherein the rod reducer further includes a second connecting arm pivotally connecting the locking sleeve with the locking lever.

10. The method according to claim 1, wherein the locking sleeve defines a longitudinal slit.

11. The method according to claim 1, wherein locking the rod into place includes sliding the outer sleeve of the taper lock bone screw into a partially locked position.

12. A method of reducing a rod into a taper lock bone screw and locking the rod into place, the method comprising:
   providing a spinal fixation system including:
      a taper lock bone screw including an inner housing and an outer housing surrounding at least a portion of the inner housing, the inner housing defining a rod receiving notch, the outer housing movable relative to the inner housing; and a rod reducer including:
- an elongate body having a bone screw grasping element;
- a rod reducing sleeve circumferentially disposed around at least a portion of the elongate body, the rod reducing sleeve including a rod contact portion;
- a rod reducing lever coupled to the rod reducing sleeve, the rod reducing lever configured to actuate the grasping element to grasp the screw and position the rod into the rod receiving notch defined in the taper lock bone screw;
- a locking sleeve circumferentially disposed around at least a portion of the rod reducing sleeve, the locking sleeve including a screw grasping structure; and
- a locking lever coupled to the locking sleeve, the locking lever configured to actuate the screw grasping structure to grasp the outer housing of the taper lock bone screw and move the outer housing into a locked position;

implanting the taper lock bone screw into a vertebral body of a subject;
placing the rod in the rod reducer;
aligning the rod reducer with the taper lock bone screw;
reducing the rod into the rod receiving notch in the inner housing of the taper lock bone screw; and
locking the rod into place.

13. The method according to claim 12, wherein locking the rod into place includes sliding the outer housing of the taper lock bone screw into a partially locked position.

14. The method according to claim 12, wherein the rod reducing lever is pivotally associated with the elongate body and the rod reducing sleeve.

15. The method according to claim 14, wherein reducing the rod into the rod receiving notch in the taper lock bone screw includes actuating the rod reducing lever causing the grasping element to grasp the taper lock bone screw and rod contact portion to position the rod into the rod receiving notch of the taper lock bone screw.

16. The method according to claim 15, wherein actuating the rod reducing lever includes aligning the rod reducing lever with the elongate body.

17. The method according to claim 12, wherein locking the rod into place includes actuating the locking lever causing the screw grasping structure to grasp and move the outer housing into a locked position.

18. The method according to claim 17, wherein actuating the locking lever includes aligning the rod reducing lever with the elongate body.

19. The method according to claim 12, wherein the rod reducer further includes a first connecting arm pivotally connecting the rod reducing lever with the rod reducing sleeve and a second connecting arm pivotally connecting the locking sleeve with the locking lever.

20. The method according to claim 12, wherein the locking sleeve defines a longitudinal slit.

* * * * *